United States Patent
Hiraike et al.

(10) Patent No.: US 7,361,776 B2
(45) Date of Patent: Apr. 22, 2008

(54) ZERO-VALENT TRANSITION METAL COMPLEX AND METHOD FOR PRODUCING AN ORGANOMETALLIC COMPOUND USING THE SAME AS A STARTING MATERIAL

(75) Inventors: Hiroshi Hiraike, Osaka (JP); Takeharu Morita, Osaka (JP); Fumiyuki Ozawa, Osaka (JP); Hiroyuki Katayama, Osaka (JP)

(73) Assignee: Sekisui Chemical Co., Ltd., Osaka-shi (JP)

( * ) Notice: Subject to any disclaimer, the term of this patent is extended or adjusted under 35 U.S.C. 154(b) by 369 days.

(21) Appl. No.: 10/543,098

(22) PCT Filed: Feb. 13, 2004

(86) PCT No.: PCT/JP2004/001589

§ 371 (c)(1),
(2), (4) Date: Jul. 22, 2005

(87) PCT Pub. No.: WO2004/072003

PCT Pub. Date: Aug. 26, 2004

(65) Prior Publication Data

US 2006/0149088 A1 Jul. 6, 2006

(30) Foreign Application Priority Data

Feb. 17, 2003 (JP) ............................ 2003-038563
Jun. 2, 2003 (JP) ............................ 2003-157141

(51) Int. Cl.
 C07F 15/00 (2006.01)
 B01J 31/00 (2006.01)
(52) U.S. Cl. .................... 556/21; 556/23; 556/136; 502/152; 502/155
(58) Field of Classification Search ............. 556/21, 556/23; 502/152, 155
See application file for complete search history.

(56) References Cited

U.S. PATENT DOCUMENTS 5,710,298 A 1/1998 Grubbs et al. ................ 556/22
5,831,108 A 11/1998 Grubbs et al. ................ 556/21
5,917,071 A * 6/1999 Grubbs et al. ................ 556/21
6,407,190 B1 6/2002 Van Der Schaaf et al. . 526/171

FOREIGN PATENT DOCUMENTS

| GB | 2 114 149 A | 8/1983 |
|----|-------------|--------|
| JP | 11-262667 | 9/1999 |
| JP | 11-510807 | 9/1999 |
| JP | 2002-506452 | 2/2002 |
| JP | 2003-286295 | 10/2003 |
| WO | 96/04289 A1 | 2/1996 |
| WO | 97/06185 A1 | 2/1997 |
| WO | 99/00396 A1 | 1/1999 |

OTHER PUBLICATIONS

P. Pertici, et al.; "A New Synthetic Method for the Preparation of Cyclo-olefin Ruthenium Complexes;" *Journal of the Chemical Society, Dalton Transitions: Inorganic Chemistry*; No. 10; 1980; pp. 1961-1964.
Supplementary European Search Report dated Oct. 7, 2007 for PCT/JP2004/001589.

* cited by examiner

*Primary Examiner*—Porfirio Nazario-Gonzalez
(74) *Attorney, Agent, or Firm*—Edwards Angell Palmer & Dodge LLP

(57) ABSTRACT

The present invention relates to a zero-valent transition metal complex which can be used as a starting material for producing a catalyst usable for producing a polyolefin by ring-opening metathesis polymerization of an olefin and an epothilone by ring-closing metathesis reaction, and a method for efficiently producing, at low cost, an organometallic compound useful as a catalyst, using the zero-valent transition metal complex as a starting material. Provided is a method for producing a zero-valent transition metal complex (C), which comprises reacting a divalent transition metal complex (A) with an olefin (B), the complex (A) being selected from the group consisting of a divalent ruthenium complex ($A^1$) and a divalent osmium complex ($A^2$), thereby obtaining a zero-valent transition metal complex (C), wherein the reaction is conducted under reducing conditions and after the reaction, the resultant crude product is extracted at high temperature using a saturated hydrocarbon as an extracting solvent. Also provided is a method for producing an organometallic compound, which comprises reacting the metal complex (C) with a specific compound (D) and a neutral ligand (E) in one step.

22 Claims, No Drawings

ZERO-VALENT TRANSITION METAL COMPLEX AND METHOD FOR PRODUCING AN ORGANOMETALLIC COMPOUND USING THE SAME AS A STARTING MATERIAL

BACKGROUND OF THE INVENTION

1. Field of the Invention

The present invention relates to a zero-valent transition metal complex and method for producing an organometallic compound using the same as a starting material, more particularly a zero-valent transition metal complex which can be used for producing a catalyst usable for producing a polyolefin by ring-opening metathesis polymerization of an olefin and an epothilone by ring-closing metathesis reaction, and a method for efficiently producing, at a low cost, an organometallic compound useful as a catalyst, using the zero-valent transition metal complex as a starting material.

2. Description of the Prior Art

Reactions proceeding in the presence of a transition metal compound have been widely used for producing various products from those of low-molecular-weight, e.g., medicines, to those of high-molecular-weight, e.g., highly functional plastics, by virtue of the catalytic actions which the complex from the transition metal compound provides.

The well-known reactions include polymerization of polyethylene or polypropylene in the presence of a Ziegler-Natta catalyst comprising titanium tetrachloride or trichloride and alkyl aluminum, polymerization of homogeneous polyolefin in the presence of a Kaminski catalyst comprising zirconocene and methyl aluminoxane, and organic metathesis reactions in the presence of a transition metal carbene catalyst.

Recently, transition metal carbene catalysts, in particular ruthenium carbene catalysts, have been attracting attention. A ruthenium carbene catalyst is composed of a compound having the Ru=C bond (which holds a ruthenium atom and chargeless, divalent carbon atom). In particular, dichloro-phenylcarbene-bis-(tricyclohexyl phosphine)ruthenium, represented by $[(Cl_2Ru=CHPh)(PCy_3)_2]$, is developed and disclosed by the Grubbs group of California Institute of Technology (refer to JP-A-11-510807, claims and the like and JP-A-11-262667, claims and the like).

It has been clearly demonstrated that the compound exhibits excellent catalytic activity for metathesis without been deactivated even in the presence of moisture or oxygen, and showing resistance to a functional group in a metathesis reaction substrate. As such, it has been widely used for various industrial purposes, e.g., ring-closing metathesis synthesis of various olefins to produce medicines or the like; and ring-opening polymerization of norbornene-based monomers, beginning with dicyclopentadiene as a representative starting monomer for metathesis polymerization, to produce formed articles of excellent characteristics with respect to mechanical strength, heat resistance and dimensional stability, among others, where the reaction is carried out in a mold in a reaction injection molding process or the like, and hence attracting attention.

The catalyst exhibits its catalytic activity not coming from its reactions with an alkyl metal or the like to activate the catalyst in the system but from the inherent activity of the single complex itself. This causes problems resulting from dispersibility or the like of the catalyst being a rate-determining step, because the reactions of a metathesis-reactive monomer start as soon as it comes into contact with the catalyst. This may cause crucial problems in polymerization of cross-linkable monomer, e.g., dicyclopentadiene. These problems include severe limitations imposed on the process operation and fluctuations of the polymer product properties.

A method for retarding the polymerization by incorporating triphenyl phosphine or the like is generally known to solve the above problems. This, however, may cause problems related to product safety, resulting from contamination of the system with phosphorus or the like.

Dichloro-phenylcarbene-bis-(tricyclohexyl phosphine)ruthenium, represented by $[(Cl_2Ru=CHSPh)(PCy_3)_2]$, is proposed as a catalyst which can solve the above problems (refer to, e.g., JP-A-2002-506452, claims and the like). The compounds of the above formula with sulfur atom substituted by oxygen atom, or imino or phosphine-diyl group are also disclosed by JP-A-2002-506452.

This catalyst, although excellent, involves process-related problems. For example, JP-A-2002-506452 discloses its synthesis methods a) and b) in EXAMPLE 1 (page 52). The method a) needs a starting material which itself has a complex chemical structure of $RuCl_2[P(C_6H_{11})_3]_2(=CH-C_6H_5)$ and hence a time-consuming process for its synthesis. On the other hand, the method b) uses ruthenium dichloride (cis,cis-cyclooctadiene) as a starting material, which itself is a compound of simple chemical structure. However, it needs a complex process for production of the target product, comprising reaction of the above compound with complex-structure compounds of 1,8-diazabicyclo[5.4.0]undeca-7-ene and tricyclohexyl phosphine in isopropanol at 80° C. for 1 hour, and incorporation of the effluent, after it is cooled at −20° C. for 1 hour, with a 1 mol/L diethyl ether hydrochloride solution with stirring for 15 minutes and further with 1-hexine and phenyl vinyl sulfide. Therefore, the process needs massive quantities of expensive starting materials and several steps, and hence is time-consuming and disadvantageous costwise.

Under these circumstances, the inventors of the present invention have studied synthesis of heterocarbene complexes, e.g., $RuCl_2[P(C_6H_{11})_3]_2(=CH-S-)$, and proposed a method for synthesizing a heterocarbene complex efficiently at a low cost using a starting material of relatively simple chemical structure (as disclosed by JP-A-2003-286295) as an alternative for the conventional method based on vinyl exchanging.

However, this method involves a problem of limited production yield, when the starting material of relatively simple chemical structure, i.e., a zero-valent transition metal complex (e.g., ruthenium(cymene)(1,5-cyclooctadiene) is to be synthesized on a commercial scale. Increasing the yield needs iteration of extraction cycles, which makes the process complex and disadvantageous costwise.

SUMMARY OF THE INVENTION

It is an object of the present invention to provide a zero-valent transition metal complex as a starting material for producing a catalyst usable for producing a polyolefin by ring-opening metathesis polymerization of an olefin and an epothilone by ring-closing metathesis reaction, in consideration of the above problems. It is another object of the present invention to provide a method for efficiently producing, at a low cost, an organometallic compound useful as a catalyst using the above complex as a starting material.

The inventors of the present invention have found, after having extensively studied to solve problems involved in the conventional methods for producing an organometallic compound, e.g., zero-valent transition metal complex, that a zero-valent transition metal complex as the target product can be efficiently synthesized in a high yield and at a low cost by hot extraction of a crude, solid reaction product containing the target product with a saturated hydrocarbon as an extracting solvent, achieving the present invention.

The first aspect of the present invention is a method for producing a zero-valent transition metal complex (C) by reacting a divalent transition metal complex (A) selected from the group consisting of a divalent ruthenium complex ($A^1$) and divalent osmium complex ($A^2$) with an olefin (B), wherein the reaction is conducted under reducing conditions and the resulting crude product is treated by hot extraction with a saturated hydrocarbon as an extracting solvent.

The second aspect of the present invention is the method of the first aspect for producing a zero-valent transition metal complex, wherein the divalent transition metal complex (A) is selected from the group consisting of a divalent ruthenium-arene complex and divalent osmium-arene complex.

The third aspect of the present invention is the method of the second aspect for producing a zero-valent transition metal complex, wherein the arene is a benzene ring substituted with an alkyl of 1 to 20 carbon atoms.

The fourth aspect of the present invention is the method of the second aspect for producing a zero-valent transition metal complex, wherein the divalent ruthenium complex ($A^1$) is a cymene ruthenium dichloride complex.

The fifth aspect of the present invention is the method of the first aspect for producing a zero-valent transition metal complex, wherein the olefin (B) is a cyclopolyene.

The sixth aspect of the present invention is the method of the fifth aspect for producing a zero-valent transition metal complex, wherein the cyclopolyene is a cyclodiene.

The seventh aspect of the present invention is the method of the first aspect for producing a zero-valent transition metal complex, wherein the reaction is conducted in an alcohol solvent in the presence of an elementary metal or metal compound as a reducing agent.

The eighth aspect of the present invention is the method of the seventh aspect for producing a zero-valent transition metal complex, wherein the metal compound is a sodium compound.

The ninth aspect of the present invention is the method of the first aspect for producing a zero-valent transition metal complex, wherein the hot extraction is conducted at 30° C. or higher.

The tenth aspect of the present invention is the method of the first aspect for producing a zero-valent transition metal complex, wherein the extracting solvent is at least one species of saturated hydrocarbon selected from the group consisting of hexane, heptane and cyclohexane.

The eleventh aspect of the present invention is the method of the fourth aspect for producing a zero-valent transition metal complex, wherein the zero-valent transition metal complex is ruthenium(cymene)(1,5-cyclooctadiene).

The twelfth aspect of the present invention is a method for producing an organometallic compound, wherein the zero-valent transition metal complex (C) produced by one of the first to $11^{th}$ methods for producing a zero-valent transition metal complex is reacted with a compound (D) represented by the general formula (1) and neutral ligand (E) in one step.

$$R^1Y^1CR^2X^1_2 \qquad (1)$$

(wherein, $R^1$ is hydrogen atom, or an alkyl group of 1 to 20 carbon atoms, alkenyl group of 2 to 20 carbon atoms or aryl group of 6 to 20 carbon atoms, each group of which may be substituted by an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 0 to 10 carbon atoms, halogen atom, or nitro, acetyl or acetoxy group; $Y^1$ is a chalcogen atom, nitrogen-containing group represented by the general formula (2) or phosphorus-containing group represented by the general formula (3); and

$X^1$ is a halogen atom, where $R^2$ and $R^3$ in the general formulae are each the same as $R^1$, and two of $R^1$ to $R^3$ may be bound to each other).

The thirteenth aspect of the present invention is the method of the twelfth aspect for producing an organometallic compound, wherein $R^2$ is hydrogen atom.

The fourteenth aspect of the present invention is the method of the twelfth aspect for producing an organometallic compound, wherein $R^1$ or $R^3$ is phenyl group, or phenyl group substituted by at least one substituent selected from the group consisting of an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 10 carbon atoms or less, halogen atom, nitro group and acetyl group.

The fifteenth aspect of the present invention is the method of the twelfth aspect for producing an organometallic compound, wherein $Y^1$ is selected from the group consisting of oxygen, sulfur and selenium atoms.

The sixteenth aspect of the present invention is the method of the twelfth aspect for producing an organometallic compound, wherein the neutral ligand (E) is selected from the group consisting of a tertiary phosphine and imidazolium-2-ylidene.

The seventeenth aspect of the present invention is the method of the twelfth aspect for producing an organometallic compound, wherein the organometallic compound is represented by the general formula (4):

(wherein, M is elementary ruthenium or osmium; $R^1$, $R^2$, $Y^1$ and $X^1$ are each the same as the respective one described before; and $L^1$s are each a neutral electron donor, which may be the same or different).

The eighteenth aspect of the present invention is the method of the seventeenth aspect for producing an organometallic compound, wherein $R^2$ is hydrogen atom.

The nineteenth aspect of the present invention is the method of the seventeenth aspect for producing an organometallic compound, wherein $R^1$ or $R^3$ is phenyl group, or phenyl group substituted by at least one substituent selected from the group consisting of an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 10 carbon atoms or less, halogen atom, nitro group and acetyl group.

The twentieth aspect of the present invention is the method of the seventeenth aspect for producing an organometallic compound, wherein $Y^1$ is selected from the group consisting of oxygen, sulfur and selenium atoms.

The twenty-first aspect of the present invention is the method of the seventeenth aspect for producing an organometallic compound, wherein the organometallic compound is dichloro[bistricyclohexylphosphino]phenylthiomethinoruthenium.

The twenty-second aspect of the present invention is the method of the seventeenth aspect for producing an organometallic compound, wherein the organometallic compound is free of an impurity of vinyl hetero compound or vinyl compound.

As described above, the present invention provides a method for producing a zero-valent transition metal complex (C) by reacting a divalent transition metal complex (A) selected from the group consisting of a divalent ruthenium complex ($A^1$) and divalent osmium complex ($A^2$) with an olefin (B), wherein the reaction is conducted under reducing conditions and the resulting crude product is treated by hot extraction with a saturated hydrocarbon as an extracting solvent, and the like. The preferred embodiments include the following.

(1) The method of the first aspect for producing a zero-valent transition metal complex, wherein the divalent osmium complex ($A^2$) is a cymene osmium dichloride complex.
(2) The method of the ninth or tenth aspect for producing a zero-valent transition metal complex, wherein the hot extraction is conducted with hexane as an extracting solvent (extracting agent) at 30 to 60° C.
(3) The method of the ninth or tenth aspect for producing a zero-valent transition metal complex, wherein the hot extraction is conducted with heptane as an extracting solvent (extracting agent) at 30 to 90° C.

DETAILED DESCRIPTION OF THE INVENTION

The method of the present invention for producing a zero-valent transition metal complex, and that for producing an organometallic compound useful as a catalyst using the metal complex as a starting material are described for each item.

First, the method for producing a zero-valent transition metal complex reacts a divalent transition metal complex (A) selected from the group consisting of a divalent ruthenium complex ($A^1$) and divalent osmium complex ($A^2$) with an olefin (B) to produce the zero-valent transition metal complex (C), wherein the reaction is conducted under reducing conditions and the resulting crude product is treated by hot extraction with a saturated hydrocarbon as an extracting solvent.

1. Divalent Transition Metal Complex (A)

In the method of the present invention for producing a zero-valent transition metal complex, a divalent transition metal complex (A) is selected from the group consisting of a divalent ruthenium complex ($A^1$) and divalent osmium complex ($A^2$). It is one of the starting materials for producing the zero-valent transition metal complex (C) as the target product of the present invention, and works to bring the central metal of the complex (C).

In the method of the present invention, a zero-valent complex as the target product cannot be produced in a high yield from a multi-valent complex, e.g., divalent ruthenium complex ($A^1$) or divalent osmium complex ($A^2$), unless the reaction is conducted under reducing conditions.

The ligand of the divalent transition metal complex (A), i.e., ruthenium complex ($A^1$) or divalent osmium complex ($A^2$), is not limited so long as it can form a transition metal complex. However, it preferably has at least one arene ligand, viewed from stability or the like of the product.

An arene ligand is coordinated in a compound having an aromatic ring, represented by benzene ring, through the π electrons on the ring. The preferable arene ligands include benzene, substituted benzene and naphthalene rings, and cyclopentadiene anion, of which substituted benzene ring is more preferable.

Substituted benzene rings include the ring substituted by an alkyl group of 1 to 20 carbon atoms or a polar group, e.g., ester. The specific examples include toluene, xylene, cumene, cymene, hexamethylbenzene and ethyl benzoate, of which cymene is more preferable than others, viewed from product stability, cost and production yield.

The specific examples of the divalent ruthenium complex ($A^1$) include cymene ruthenium dichloride, benzene ruthenium dichloride, hexamethylbenzene ruthenium dichloride, ethyl benzoate ruthenium dichloride, cumene ruthenium dichloride, naphthalene ruthenium dichloride complexes, of which cymene ruthenium dichloride and benzene ruthenium dichloride complexes are more preferable.

The specific examples of the divalent osmium complex ($A^2$) include cymene osmium dichloride, benzene osmium dichloride, hexamethylbenzene osmium dichloride, ethyl benzoate osmium dichloride, cumene osmium dichloride, naphthalene osmium dichloride complexes, of which cymene osmium dichloride and benzene osmium dichloride complexes are more preferable.

2. Olefin (B)

For production of a zero-valent transition metal complex (C) as the target product of the present invention, it is preferable to use an arene and olefin ligands simultaneously, viewed from stability and reactivity of the complex. For this reason, an olefin (B) is used as one of the starting materials for the complex (C).

The examples of olefins (B) useful for the olefin ligand include monoolefins (e.g., ethylene), dienes (e.g., butadiene and cyclohexadiene) and trienes (e.g., cyclooctatriene). When a monoolefin is used, it is preferably a bimolecular coordination type in consideration of saturation electron number.

A cyclopolyene is more preferable, viewed from stability and reactivity of the zero-valent transition metal complex. More specifically, the useful cyclopolyenes include 1,3-cyclohexadiene, 1,4-cyclohexadiene, 1,3-cyclooctadiene, 1,5-cyclooctadiene, α-terpinene and other cyclodienes, e.g., substituted compounds of the above dienes, and cyclotrienes, e.g., 1,3,5-cyclooctatriene and 1,3,5-cycloheptatriene. Of these, cyclodienes are more preferable viewed from stability of the complex as the target product, still more preferably 1,5-cyclooctadiene viewed from stability and production yield of the complex.

3. Method for Producing a Zero-valent Transition Metal Complex (C)

As described above, the method of the present invention is to produce a zero-valent complex as the target product from a multi-valent compound, e.g., divalent ruthenium complex ($A^1$) or divalent osmium complex ($A^2$) and olefin (B). Therefore, the target product cannot be produced in a high yield, unless the reaction is conducted under reducing conditions.

The reaction is preferably conducted in an alcohol solvent in the presence of a metallic compound as a reducing agent to realize a reducing atmosphere. More specifically, the metallic compound working as a reducing agent preferably contains zinc or a typical element. In particular, the compound containing sodium is more preferable viewed from handleability and cost. Still more specifically, sodium carbonate and sodium hydrogen carbonate are the preferable compounds.

In order to efficiently conduct the reduction, it is preferable to incorporate a sodium-containing compound as a reducing agent at 1 equivalent or more per equivalent of ruthenium or osmium. However, use of an excessive quantity of reducing agent is undesirable, viewed from removal of the agent from the effluent stream and operating cost. Therefore, it is preferably incorporated at 0.5 to 10 equivalents per equivalent of ruthenium or osmium, more preferably 1 to 5 equivalents.

Alcohol for realizing a reducing condition is not limited so long as it is kept liquid under the reaction conditions. However, it is preferably methanol, ethanol, isopropyl alcohol or the like viewed from cost, handleability, among others.

For the reaction conditions, under reflux of alcohol, e.g., ethanol, the reaction system is operated at about 90° C. for 1 to 20 hours under reflux, preferably with stirring, to enhance reaction efficiency.

In the present invention, it is necessary to remove the reducing agent and by-products, when the synthesis reaction process is completed, from the effluent solution, or from the crude, solid reaction product containing the target product. Hot extraction of the solid product can enhance yield of the target product.

The crude, solid reaction product containing the target product can be separated from the effluent solution by a common solid/liquid separation method, e.g., evaporation (or filtration) of the liquid phase. The effluent solution, in which the reducing agent and by-products are partly precipitated, may be directly treated by evaporation to recover the target product from the resulting clay-like solid by hot extraction. In other words, the effluent solution may be totally solidified once without being subjected to solid/liquid separation and then the target product is recovered therefrom by hot extraction.

The zero-valent transition metal complex as the target product is separated from the crude, solid product of the synthesis reaction by hot extraction, conducted preferably at 30° C. or higher, more preferably 40° C. or higher. The upper extraction temperature limit is adequately set depending on boiling point, distribution coefficient and mass transfer rate of the extracting solvent used. It is normally about 10° C. lower than boiling point of the extracting solvent. Extraction temperature is limited by boiling point of the solvent, and stability of the system or solute, although increasing temperature increases diffusion rate (diffusion of mass into the solid inside, or the like). Extraction time is 10 minutes to 5 hours, preferably 30 minutes to 3 hours. Extraction temperature below 30° C. is not practical on a commercial scale, because of deteriorated extraction efficiency and greatly extended extraction time. The extraction treatment may be conducted with stirring to enhance extraction efficiency (or contacting efficiency).

An anionic compound contained in the starting material is left in a by-product. The extracting solvent (extracting agent) is preferably a saturated hydrocarbon of high solubility and selectivity to selectively dissolve the zero-valent transition metal complex as the target product while keeping the by-product or impurity undissolved. Most preferable saturated hydrocarbons include hexane (boiling point: 68.7° C.), heptane (boiling point: 98.4° C.) and cyclohexane (boiling point: 80° C.).

A series of the synthesis reactions and subsequent hot extraction are preferably conducted in an inert atmosphere to prevent oxygen and other reactive compounds from coming into contact with the zero-valent transition metal complex.

When the synthesis method of the present invention is adopted, it may be most preferable to produce a ruthenium (cymene)(1,5-cyclooctadiene) complex, viewed from production yield and stability of the complex and cost.

4. Zero-valent Transition Metal Complex (C)

The zero-valent transition metal complex (C) produced by the synthesis method of the present invention can be used as a starting material for producing a catalyst usable for producing a polyolefin by ring-opening metathesis polymerization of an olefin and an epothilone by ring-closing metathesis reaction, and works to bring the central metal of the catalyst (organometallic compound).

The central metal in the zero-valent transition metal complex (C) is not limited so long as it can form a transition metal complex. It is however preferably a transition metal of VIA, VIIA, VIII or IB group. Of these, ruthenium or osmium is particularly preferable for the present invention, viewed from reactivity, usefulness or the like.

The method of the present invention for producing the zero-valent transition metal complex (C) uses a divalent complex of ruthenium or osmium as the starting material of divalent transition metal complex (A), but a divalent complex of another transition metal described above may be used.

The ligand for the zero-valent transition metal complex (C) is not limited so long as it generally forms a transition metal complex. Of the ligands, however, a combination of arene (aromatic hydrocarbon) and olefin ligands is preferable viewed from stability and reactivity of the complex. Therefore, the synthesis method of the present invention uses a divalent ruthenium-arene complex or divalent osmium-arene complex for the divalent transition metal complex (A) as one of the starting materials, and also uses an olefin ligand for the olefin (B) as the other starting material.

The zero-valent transition metal complex (C) is adequately synthesized by selecting the divalent transition metal complex (A) and olefin (B). The examples of the zero-valent transition metal complex include the following, where a valence number and chemical formula are indicated in the parentheses ( ) and [ ] for each compound.

1. ($\eta^6$-benzene)($\eta^4$-1,3-cyclohexadiene)ruthenium (0), [Ru($\eta^6$-$C_6H_6$)($\eta^4$-1,3-$C_6H_8$)]
2. ($\eta^6$-benzene)($\eta^4$-1,5-cyclooctadiene)ruthenium (0), [Ru($\eta^6$-$C_6H_6$)($\eta^4$-1,5-$C_8H_{12}$)]
3. ($\eta^6$-cymene)($\eta^4$-1,5-cyclooctadiene)ruthenium (0), [Ru{$\eta^6$-CH($CH_3$)$_2C_6H_4CH_3$}($\eta^4$-1,5-$C_8H_{12}$)]
4. ($\eta^6$-naphthalene)($\eta^4$-1,5-cyclooctadiene)ruthenium (0), [Ru($\eta^6$-$C_{10}H_8$)($\eta^4$-1,5-$C_8H_{12}$)]
5. ($\eta^6$-cymene)($\eta^4$-α-terpinene)ruthenium (0), [Ru($\eta^6$-CH($CH_3$)$_2C_6H_4CH_3$)($\eta^4$-α-terpinene)]

6. (η⁶-cymene)bis(ethylene)ruthenium (0), [Ru{η⁶-CH(CH₃)₂C₆H₄CH₃}(C₂H₄)₂]
7. (η⁶-cymene)(η⁴-1,3-cyclohexadiene)ruthenium (0), [Ru{η⁶-CH(CH₃)₂C₆H₄CH₃}(η⁴-1,3-C₆H₈)]
8. (η⁶-ethyl benzoate)(η⁴-1,5-cyclooctadiene)ruthenium (0), [Ru{η⁶-C₆H₅COOEt}(η⁴-1,5-C₈H₁₂)]
9. (η⁶-hexamethylbenzene)(η⁴-1,5-cyclooctadiene)ruthenium (0), [Ru{η⁶-C₆Me₆}(η⁴-1,5-C₈H₁₂)]
10. (η⁶-benzene)(η⁴-1,3-cyclohexadiene)osmium (0), [Os(η⁶-C₆H₆)(η⁴-1,3-C₆H₈)]
11. (η⁶-benzene)(η⁴-1,3-cyclooctadiene)osmium (0), [Os(η⁶-C₆H₆)(η⁴-1,5-C₈H₁₂)]
12. (η⁶-cymene)(η⁴-1,5-cyclooctadiene)osmium (0), [Os{η⁶-CH(CH₃)₂C₆H₄CH₃}(η⁴-1,5-C₈H₁₂)]
13. (η⁶-naphthalene)(η⁴-1,5-cyclooctadiene)osmium (0), [Os(η⁶-C₁₀H₈)(η⁴-1,5-C₈H₁₂)]
14. (η⁶-cymene)(η⁴-α-terpinene)osmium (0), [Os(η⁶-CH(CH₃)₂C₆H₄CH₃)(η⁴-α-terpinene)]
15. (η⁶-cymene)bis(ethylene)osmium (0), [Os{η⁶-CH(CH₃)₂C₆H₄CH₃}(C₂H₄)₂]
16. (η⁶-ethyl benzoate)(η⁴-1,5-cyclooctadiene)osmium (0), [Os{η⁶-C₆H₅COOEt}(η⁴-1,5-C₈H₁₂)]
17. (η⁶-hexamethylbenzene)(η⁴-1,5-cyclooctadiene)osmium (0), [Os{η⁶-C₆Me₆}(η⁴-1,5-C₈H₁₂)]

Of the above zero-valent transition metal complexes (C), the more preferable ones viewed from stability and production cost are (η⁶-benzene)(η⁴-1,3-cyclohexadiene)ruthenium (0), (η⁶-benzene)(η⁴-1,5-cyclooctadiene)ruthenium (0), (η⁶-cymene)(η⁴-1,5-cyclooctadiene)ruthenium (0), (η⁶-naphthalene)(η⁴-1,5-cyclooctadiene)ruthenium (0) and (η⁶-ethyl benzoate)(η⁴-1,5-cyclooctadiene)ruthenium (0), and the still more preferable ones are (η⁶-benzene)(η⁴-1,5-cyclooctadiene)ruthenium (0) and (η⁶-cymene)(η⁴-1,5-cyclooctadiene)ruthenium (0).

The zero-valent transition metal complex (C) produced by the synthesis method of the present invention is suitably used as a starting material for producing an organometallic compound working as a catalyst, e.g., heterocarbene complex of RuCl₂[P(C₆H₁₁)₃]₂(=CH—S—R).

5. Compound (D)

One of the embodiments of the zero-valent transition metal complex (C) of the present invention is a starting material for producing the above-described organometallic compound useful as a catalyst, e.g., heterocarbene complex. The method for producing the organometallic compound reacts the zero-valent transition metal complex (C) produced by the synthesis method of the present invention with a compound (D) represented by the general formula (1) and neutral ligand (E) in one step.

The compound (D) for the present invention is used as one of the starting materials for an organometallic compound useful as a catalyst, and works to bring an anionic ligand, e.g., halogen atom, which is directly bound to the metal in the organometallic compound, and an electron donorable group, e.g., phenylthio or phenyl ether group, which is directly bound to the carbene (chargeless, divalent carbon atom) in the organometallic compound.

$$R^1Y^1CR^2X^1_2 \quad (1)$$

(wherein, R¹ is hydrogen atom, or an alkyl group of 1 to 20 carbon atoms, alkenyl group of 2 to 20 carbon atoms or aryl group of 6 to 20 carbon atoms, each group of which may be substituted by an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 0 to 10 carbon atoms, halogen atom, or nitro, acetyl or acetoxy group; Y¹ is a chalcogen atom, nitrogen-containing group represented by the general formula (2) or phosphorus-containing group represented by the general formula (3); and

(2)

(3)

X¹ is a halogen atom, where R² and R³ in the general formulae are each the same as R¹, and two of R¹ to R³ may be bound to each other).

The compound (D) for the present invention is not limited, so long as it is represented by the general formula (1). In the formula (1), however, R² is preferably hydrogen atom. It is particularly preferably that R¹ and R³ are phenyl group, or phenyl group substituted by at least one substituent selected from the group consisting of an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 10 carbon atoms or less, halogen atom, nitro group and acetyl group, and Y¹ is selected from the group consisting of oxygen, sulfur and selenium atoms, viewed from reactivity, usefulness and the like.

More specifically, the examples of the compound (D) for the present invention include the following, where the chemical formula is indicated in the parentheses [ ] for each compound.

1. Dichloromethylphenyl sulfide, [Ph-S—CHCl₂]
2. Dichloromethylphenyl selenide, [Ph-Se—CHCl₂]
3. Dichloromethylphenyl phosphine, [Ph-PH—CHCl₂]
4. Dichloromethylphenylamine, [Ph-NH—CHCl₂]
5. (Phenyldichloromethyl)phenyl sulfide, [Ph-S—C(Ph)Cl₂]
6. Dichloromethyl-p-tolyl sulfide, [p-tolyl-S—CHCl₂]
7. Dichloromethyl-p-chlorophenyl sulfide, [p-Cl-Ph-S—CHCl₂]
8. Dichloromethyl-p-methoxyphenyl sulfide, [p-MeO-Ph-S—CHCl₂]
9. Dichloromethylbenzyl sulfide, [Benzyl-S—CHCl₂]
10. Dichloromethylisopropyl sulfide, [i-Pr—S—CHCl₂]
11. N-dichloromethylcarbazole,

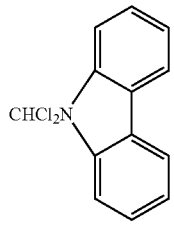

12. N-dichloromethylpyrrolidinone,

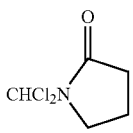

13. N-dichloromethylphthalimide,

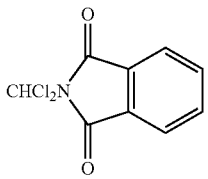

and
14. N-dichloromethylpyrrolidine.

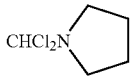

6. Neutral Ligand (E)

The neutral ligand (E) for the present invention is a neutral electron donor, serving as one of the starting materials for an organometallic compound useful as a catalyst. It works to bring the neutral ligand directly coordinated with the metal in the organometallic compound.

The neutral ligand (E) is not limited, so long as it is a neutral electron donor. However, it is preferably a tertiary phosphine or imidazolium-2-ylidene.

The tertiary phosphines useful for the present invention include the one represented by the formula $PR^6R^7R^8$.

Wherein, $R^6$, $R^7$ and $R^8$ are each an alkyl group of 1 to 20 carbon atoms or aryl group of 6 to 20 carbon atoms, preferably selected from the group consisting of methyl, ethyl, isopropyl, t-butyl, cyclohexyl, phenyl and substituted phenyl groups. They may be the same or different.

The tertiary phosphine may be of a bidentate ligand type, e.g., bisphosphine.

More specifically, the examples of the tertiary phosphine for the present invention include the following, where the chemical formula is indicated in the parentheses [ ] for each compound.
1. Tricyclopentyl phosphine, [$P(C_5H_9)_3$]
2. Tricyclohexyl phosphine, [$P(C_6H_{11})_3$]
3. Triethyl phosphine, [$P(C_2H_5)_3$]
4. Trimethyl phosphine, [$P(CH_3)_3$]
5. Triisopropyl phosphine, [$P\{CH(CH_3)_2\}_3$]
6. Tripropyl phosphine, [$P(CH_2CH_2CH_3)_3$]
7. Tributyl phosphine, [$P(CH_2CH_2CH_2CH_3)_3$]
8. Triphenyl phosphine, [$PPh_3$]
9. Ethylenebis(diphenyl phosphine), [$Ph_2PCH_2CH_2PPh_2$]
10. Ethylenebis(diisopropyl phosphine), [$\{(CH_3)_2CH\}_2PCH_2CH_2P\{CH(CH_3)\}_2$]
11. Ethylenebis(dicyclopentyl phosphine), [$(C_5H_9)_2PCH_2CH_2P(C_5H_9)_2$]
12. Ethylenebis(dicyclohexyl phosphine), [$(C_6H_{11})_2PCH_2CH_2P(C_6H_{11})_2$]

Preferable imidazolium-2-ylidene compounds are imidazoline-2-ylidene derivatives and 4,5-dihydro imidazoline-2-ylidene derivatives. More specifically, they include N',N'-dimesitylimidazoline-2-ylidene and N',N'-dimesityl-4,5-dihydroimidazoline-2-ylidene ligands.

7. Organometallic Compound and its Production Method

The organometallic compound for the present invention, useful as a catalyst, is produced by the method in which the zero-valent transition metal complex (C) as the starting material is reacted with the compound (D) and neutral ligand (E) in one step.

The organometallic compound is not limited so long as it is produced by the above method. However, it is preferably a compound represented by the general formula (4).

(4)

(Wherein, M is a transition metal element; $R^1$, $R^2$, $Y^1$ and $X^1$ are each the same as the respective one described before, and $L^1$s are each a neutral electron donor, which may be the same or different).

Of the organometallic compounds, in particular, the optimum compounds are the following viewed from reactivity, usefulness and the like; in the general formula (4), M is ruthenium or osmium; $R^2$ is hydrogen atom; $R^1$ is phenyl group, or phenyl group substituted by at least one substituent selected from the group consisting of an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 10 carbon atoms or less, halogen atom, nitro group and acetyl group; and $Y^1$ is selected from the group consisting of oxygen, sulfur and selenium atoms, viewed from reactivity, usefulness and the like.

Moreover, the particularly preferable ones viewed from stability, usefulness and production cost of the product are those having M of ruthenium, $R^2$ of hydrogen atom, $X^1$ of chlorine, $Y^1$ of sulfur or selenium, and $R^1$ of phenyl or the substituted phenyl group described above.

When $Y^1$ is a hetero atom, e.g., sulfur, selenium or nitrogen, the produced organometallic compound is excellent in thermal stability by virtue of π electron donorability provided by the element, bringing an advantage of producing the target product in a high yield, because the reaction can be conducted at a higher temperature.

One of the characteristics of the method of the present invention for producing an organometallic compound is use of the compound (D), represented by the general formula (1), as a reaction reagent. It is resistant to heat and light, and allows the synthesis to be conducted under various conditions.

The method of the present invention for producing an organometallic compound generally involves the reactions of the compounds (C), (D) and (E) as the three starting materials, conducted in a solvent at a temperature controlled at −78 to 150° C., preferably −10 to 110° C., with stirring as required in a nitrogen atmosphere in one step; evaporation of the effluent stream, when the reaction process is completed, to remove the solvent; and recovering and washing the solid separated from the stream to isolate the complex.

The solvent for the reaction process is not limited. However, the preferable ones, viewed from solubility include toluene, benzene, methylene chloride, chloroform, methanol, ethanol, isopropyl alcohol, tetrahydrofuran, diethyl ether and acetonitrile.

The method for producing an organometallic compound needs no reducing agent, because the reaction proceeds by merely mixing the starting materials.

The washing solvent is not limited so long as it does not decompose the complex produced. It preferably dissolves impurities more than the complex. Specifically, the preferable ones include saturated hydrocarbons, e.g., hexane and pentane, and alcohol-based solvents. It should be noted, however, that it may dissolve the complex depending on its structure, and increasing the washing effect can possibly deteriorate production yield. In such a case, the solvent is preferably cooled.

The complex is highly soluble in the solvent, in particular when the neutral ligand (E) has a saturated hydrocarbon group. Therefore, the complex product of high purity can be produced without deteriorating the yield, when it is washed with cooled hexane, pentane, methanol or the like.

The washing solvent is preferably kept at its melting point to 0° C., more preferably −78 to 0° C. to which it can be cooled with dry ice for practical purposes.

EXAMPLES

The present invention is described in more detail by EXAMPLES, which by no means limit the present invention. It is to be understood that any embodiment which utilizes the technical concept of the present invention is within the scope of the present invention.

Example 1

A 500 mL Schlenk flask, purged with nitrogen, was charged with 15 g of cymene ruthenium dichloride complex (Ru: 49 mmols), to which 150 mL of distilled ethanol (desiccant: Mg) was added. Then, the flask was charged with 50 mL (407 mmols) of 1,5-cyclooctadiene by a syringe, and then with 15 g (141 mmols) of sodium carbonate. These compounds were allowed to react with each other at 90° C. under reflux of ethanol The reaction mixture was stirred for 12 hours, and the effluent was treated by evaporation to remove the volatile components and to recover the solid, brown in color.

The solid was heated at 40° C. for 1 hour with stirring in the presence of 100 mL of hexane. The effluent solution was filtered, and the separated residua was washed with 20 mL of hexane and filtered. The resulting brownish solution was treated by evaporation to recover the solid, brownish red in color.

The recovered solid was confirmed by NMR analysis to be the target product, i.e., ruthenium(cymene)(1,5-cyclooctadiene) complex as a zero-valent transition metal complex [another name: Ru($\eta^6$-p-cymene)($\eta^4$-1,5-cyclooctadiene)]. In EXAMPLE 1, 15.3 g of the target product was recovered in a yield of 91%.

Example 2

A 100 mL Schlenk flask, purged with nitrogen, was charged with 1.53 g of cymene ruthenium dichloride complex (Ru: 5 mmols), to which 50 mL of distilled ethanol (desiccant: Mg) was added. Then, the flask was charged with 5 mL (40.7 mmols) of 1,5-cyclooctadiene by a syringe, and then with 1.5 g (14.1 mmols) of sodium carbonate. These compounds were allowed to react with each other under reflux of ethanol The reaction mixture was stirred for 3 hours, and the effluent was treated by evaporation to remove the volatile components and to recover the solid, brown in color.

The solid was heated at 40° C. for 1 hour with stirring in the presence of 100 mL of hexane. The effluent solution was filtered, and the separated residua was washed with 20 mL of hexane and filtered. The resulting brownish solution was treated by evaporation to recover the solid, brownish red in color.

The recovered solid was confirmed by NMR analysis to be the target product, i.e., ruthenium(cymene)(1,5-cyclooctadiene) complex as a zero-valent transition metal complex [another name: Ru($\eta^6$-p-cymene)($\eta^4$-1,5-cyclooctadiene)]. In EXAMPLE 2, 1.52 g of the target product was recovered in a yield of 89%. The synthesis results are given in Table 1.

Example 3

The test was carried out in the same manner as in EXAMPLE 2, except that 1,3-cyclohexadiene was used as an olefin (B). The synthesis results are given in Table 1.

Example 4

The test was carried out in the same manner as in EXAMPLE 2, except that ethylene was used as an olefin (B) and the reaction was conducted with ethylene bubbling. The synthesis results are given in Table 1.

Example 5

The test was carried out in the same manner as in EXAMPLE 2, except that ($\eta^6$-hexamethylbenzene)ruthenium dichloride (II) was used as a divalent transition metal complex (A). The results are given in Table 1.

Example 6

The test was carried out in the same manner as in EXAMPLE 2, except that ($\eta^6$-benzene)ruthenium dichloride (II) was used as a divalent transition metal complex (A). The results are given in Table 1.

Example 7

The test was carried out in the same manner as in EXAMPLE 6, except that 1,3-cyclohexadiene was used as an olefin (B). The results are given in Table 1.

Example 8

The test was carried out in the same manner as in EXAMPLE 2, except that ($\eta^6$-ethyl benzoate)ruthenium dichloride (II) was used as a divalent transition metal complex (A). The results are given in Table 1.

Example 9

The test was carried out in the same manner as in EXAMPLE 2, except that ($\eta^6$-p-cymene)osmium dichloride (II) was used as a divalent transition metal complex (A). The results are given in Table 1.

TABLE 1

|  | Divalent complex (A) | Olefin (B) | Zero-valent transition metal complex (C) | Yield (%) |
|---|---|---|---|---|
| EXAMPLE 2 | (1) | (I) | (a) | 89 |
| EXAMPLE 3 | (1) | (II) | (b) | 61 |
| EXAMPLE 4 | (1) | (III) | (c) | 66 |
| EXAMPLE 5 | (2) | (I) | (d) | 85 |
| EXAMPLE 6 | (3) | (I) | (e) | 66 |
| EXAMPLE 7 | (3) | (II) | (f) | 61 |
| EXAMPLE 8 | (4) | (I) | (g) | 78 |
| EXAMPLE 9 | (5) | (I) | (h) | 88 |

Divalent Complex (A)
(1): ($\eta^6$-p-cymene)ruthenium dichloride (II)
(2): ($\eta^6$-hexamethylbenzene)ruthenium dichloride (II)
(3): ($\eta^6$-benzene)ruthenium dichloride (II)
(4): ($\eta^6$-ethyl benzoate)ruthenium dichloride (II)
(5): ($\eta^6$-p-cymene)osmium dichloride (II)

Olefin (B)
(I): 1,5-cyclooctadiene
(II): 1,3-cyclohexadiene
(III): Ethylene

Zero-valent Transition Metal Complex (C)
(a): ($\eta^6$-p-cymene)(1,5-cyclooctadiene)ruthenium (0)
(b): ($\eta^6$-p-cymene)(1,3-cyclohexadiene)ruthenium (0)
(c): ($\eta^6$-p-cymene)(bisethylene)ruthenium (0)
(d): ($\eta^6$-hexamethylbenzene)(1,5-cyclooctadiene)ruthenium (0)
(e): ($\eta^6$-benzene)(1,5-cyclooctadiene)ruthenium (0)
(f): ($\eta^6$-benzene)(1,3-cyclohexadiene)ruthenium (0)
(g): ($\eta^6$-ethyl benzoate)(1,5-cyclooctadiene)ruthenium (0)
(h): ($\eta^6$-p-cymene)(1,5-cyclooctadiene)osmium (0)

Evaluation Results

EXAMPLES 1 and 2 produced satisfactory results, realizing a high production yield of about 90%. EXAMPLES 3 to 9, which used various divalent transition metal complexes (A) and olefins (B), also realized high production yields.

Examples 10 and 11

The test was carried out in the same manner as in EXAMPLE 2, except that sodium carbonate as a reducing agent was incorporated at a different equivalent ratio. The results are given in Table 2.

Example 12

The test was carried out in the same manner as in EXAMPLE 2, except that powdered zinc was used as a reducing agent. The results are given in Table 2.

Example 13

The test was carried out in the same manner as in EXAMPLE 2, except that the extraction was conducted at 50° C. The results are given in Table 2.

Example 14

The test was carried out in the same manner as in EXAMPLE 2, except that heptane was used as an extracting solvent. The results are given in Table 2.

Comparative Example 1

The test was carried out in the same manner as in EXAMPLE 2, except that the extraction was conducted at 25° C. The results are given in Table 2.

Comparative Example 2

The test was carried out in the same manner as in EXAMPLE 2, except that THF was used as an extracting solvent. The results are given in Table 2.

Comparative Example 3

The test was carried out in the same manner as in EXAMPLE 2, except that benzene was used as an extracting solvent. The results are given in Table 2.

TABLE 2

|  | Reducing agent (equivalents per equivalent of Ru) | Extraction temperature (° C.) | Extracting solvent | Yield (%) |
|---|---|---|---|---|
| EXAMPLE 2 | Sodium carbonate(2.8) | 40 | Hexane | 89 |
| EXAMPLE 10 | Sodium carbonate(1.0) | 40 | Hexane | 65 |
| EXAMPLE 11 | Sodium carbonate(5.0) | 40 | Hexane | 89 |
| EXAMPLE 12 | Zinc(5.0) | 40 | Hexane | 61 |
| EXAMPLE 13 | Sodium carbonate(2.8) | 50 | Hexane | 89 |
| EXAMPLE 14 | Sodium carbonate(2.8) | 40 | Heptane | 88 |
| COMPARATIVE EXAMPLE 1 | Sodium carbonate(2.8) | 25 | Hexane | 46 |
| COMPARATIVE EXAMPLE 2 | Sodium carbonate(2.8) | 40 | THF | Decomposed |
| COMPARATIVE EXAMPLE 3 | Sodium carbonate(2.8) | 40 | Benzene | Containing impurities |

Evaluation Results

EXAMPLES 1 and 2 produced satisfactory results, realizing a high production yield of about 90%. Comparing the results of EXAMPLE 2 to those of COMPARATIVE EXAMPLE 1, in particular, increasing temperature from room temperature (25° C.) to 40° C. for the extraction of the zero-valent transition metal complex for 1 hour with hexane increased the yield from 46 to 89%.

A highly polar extracting solvent of THF was confirmed to decompose the product complex (COMPARATIVE EXAMPLE 2). Benzene was confirmed to extract other components (COMPARATIVE EXAMPLE 3). On the other hand, a saturated hydrocarbon, e.g., hexane or heptane, was confirmed to efficiently extract the target product. It was also confirmed that sodium carbonate as a reducing agent gave the target product in a high yield at 2.8 equivalents per equivalent of Ru, but its effect was no longer observed notably when the equivalent ratio was increased to 5.

Examples 15 to 22

In each of EXAMPLES 15 to 22, the zero-valent transition metal complex (C) prepared in one of EXAMPLES 2 to 9 was reacted with 0.012 mols of a neutral ligand (E) and 0.006 mols of a compound (D) represented by the formula $R^1Y^1CHCl_2$, each per 0.006 mols of the complex (C), in a 100 mL flask in the presence of 20 g of toluene at 60° C. for 12 hours in a flow of nitrogen. On completion of the reaction, the effluent was treated by evaporation to remove the volatile components and to recover the solid, which was washed with methanol at −40° C. to isolate the organometallic compound. The results are given in Table 3, which also describes the zero-valent transition metal complexes (C), compounds (D) and neutral ligands (E).

TABLE 3

| | Zero-valent transition metal complex (C) | Neutral ligand (E) | $R^1$ | $Y^1$ | Yield (1) (%) | Yield (2) (%) | Target product |
|---|---|---|---|---|---|---|---|
| EXAMPLE 15 | (a) | PCy₃ | Ph | S | 91 | 81 | Formula (i) |
| EXAMPLE 16 | (a) | PiPr₃ | Ph | S | 88 | 78 | Formula (ii) |
| EXAMPLE 17 | (a) | PCy₃ | tol | S | 87 | 77 | Formula (iii) |
| EXAMPLE 18 | (a) | PCy₃ | Ph | Se | 82 | 73 | Formula (iv) |
| EXAMPLE 19 | (b) | PCy₃ | Ph | S | 68 | 41 | Formula (i) |
| EXAMPLE 20 | (e) | PCy₃ | Ph | S | 74 | 49 | Formula (i) |
| EXAMPLE 21 | (f) | PCy₃ | Ph | S | 87 | 53 | Formula (i) |
| EXAMPLE 22 | (h) | PCy₃ | Ph | S | 65 | 57 | Formula (v) |

Zero-valent Transition Metal Complex
(a): ($\eta^6$-p-cymene)(1,5-cyclooctadiene)ruthenium (0)
(b): ($\eta^6$-p-cymene)(1,3-cyclohexadiene)ruthenium (0)
(e): ($\eta^6$-benzene)(1,5-cyclooctadiene)ruthenium (0)
(f): ($\eta^6$-benzene)(1,3-cyclohexadiene)ruthenium (0)
(h): ($\eta^6$-p-cymene)(1,5-cyclooctadiene)osmium (0)

Neutral Ligand
  PCy₃: tricyclohexyl phosphine
  PiPr₃: Triisopropyl phosphine
$R^1$
  tol: p-Me-Ph group
Yield (1): Yield on the zero-valent transition metal complex (C)
Yield (2): Total yield on the divalent complex (A)

The organometallic compounds produced in EXAMPLES 15 to 22 are described below by the chemical formulae [(i) to (v)].

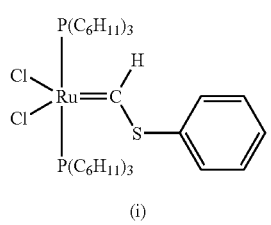

Formula (i)

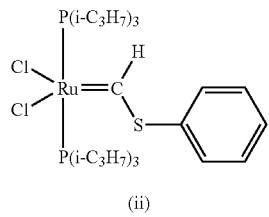

Formula (ii)

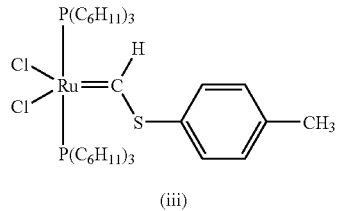

Formula (iii)

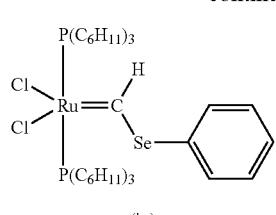

Formula (iv)

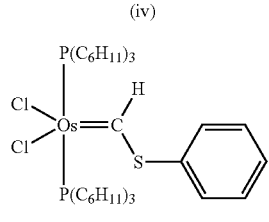

Formula (v)

Evaluation Results

It is confirmed, as shown in Table 3, that each of the zero-valent transition metal complexes efficiently gives the thiocarbene complex and that the (p-cymene)(1,5-cyclooctadiene)ruthenium dichloride complex, in particular, gives the thiocarbene complex in a high yield of 81% on the starting material of p-cymene ruthenium dichloride.

It is confirmed that the synthesis method of the present invention for producing a zero-valent transition metal complex produces, in a very high yield and at a low cost, a zero-valent transition metal complex (C) by reacting a divalent transition metal complex (A) selected from the group consisting of a divalent ruthenium complex ($A^1$) and divalent osmium complex ($A^2$) with an olefin (B). Therefore, it is a suitable method for producing a zero-valent transition metal complex (C) on a commercial scale.

The zero-valent transition metal complex produced by the synthesis method of the present invention can be used as a starting material for producing an organometallic compound, e.g., a hetero carbene complex, useful as a catalyst for producing a polyolefin by ring-opening metathesis polymerization of an olefin having a strain in the molecular structure, e.g., dicyclopentadiene, and an epothilone by ring-closing metathesis reaction.

Moreover, the synthesis method of the present invention for producing an organometallic compound can easily isolate the organometallic compound of high activity from the reaction effluent solution without causing contamination with a vinyl hetero compound or exchanged vinyl compound, which may remain as an impurity in the product produced by a conventional method. When used as a catalyst for polymerization of a norbornene-based monomer, the organometallic compound can bring an effect of very high polymerization yield.

What is claimed is:

1. A method for producing a zero-valent transition metal complex (C) by reacting a divalent transition metal complex (A) selected from the group consisting of a divalent ruthenium complex ($A^1$) and divalent osmium complex ($A^2$) with an olefin (B), wherein the reaction is conducted under reducing conditions and the resulting crude product is treated by hot extraction with a saturated hydrocarbon as an extracting solvent.

2. The method according to claim 1 for producing a zero-valent transition metal complex, wherein the divalent transition metal complex (A) is selected from the group consisting of a divalent ruthenium-arene complex and divalent osmium-arene complex.

3. The method according to claim 2 for producing a zero-valent transition metal complex, wherein the arene is a benzene ring substituted with an alkyl of 1 to 20 carbon atoms.

4. The method according to claim 2 for producing a zero-valent transition metal complex, wherein the divalent ruthenium complex ($A^1$) is a cymene ruthenium dichloride complex.

5. The method according to claim 1 for producing a zero-valent transition metal complex, wherein the olefin (B) is a cyclopolyene.

6. The method according to claim 5 for producing a zero-valent transition metal complex, wherein the cyclopolyene is a cyclodiene.

7. The method according to claim 1 for producing a zero-valent transition metal complex, wherein the reaction is conducted in an alcohol solvent in the presence of an elementary metal or metal compound as a reducing agent.

8. The method according to claim 7 for producing a zero-valent transition metal complex, wherein the metal compound is a sodium compound.

9. The method according to claim 1 for producing a zero-valent transition metal complex, wherein the hot extraction is conducted at 30° C. or higher.

10. The method according to claim 1 for producing a zero-valent transition metal complex, wherein the saturated hydrocarbon is selected from the group consisting of hexane, heptane and cyclohexane.

11. The method according to claim 4 for producing a zero-valent transition metal complex, wherein the zero-valent transition metal complex is ruthenium (cymene) (1,5-cyclooctadiene).

12. A method for producing an organometallic compound, wherein the zero-valent transition metal complex (C) produced by claim 1 is reacted with a compound (D) represented by the general formula (1) and neutral ligand (E) in one step:

$$R^1Y^1CR^2X^1_2 \quad (1)$$

(wherein, $R^1$ is hydrogen atom, or an alkyl group of 1 to 20 carbon atoms, alkenyl group of 2 to 20 carbon atoms or aryl group of 6 to 20 carbon atoms, each group of which may be substituted by an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 0 to 10 carbon atoms, halogen atom, or nitro, acetyl or acetoxy group; $Y^1$ is a chalcogen atom, nitrogen-containing group represented by the general formula (2) or phosphorus-containing group represented by the general formula (3); and

$X^1$ is a halogen atom, where $R^2$ and $R^3$ in the general formulae are each the same as $R^1$, and two of $R^1$ to $R^3$ may be bound to each other).

13. The method according to claim 12 for producing an organometallic compound, wherein $R^2$ is hydrogen atom.

14. The method according to claim 12 for producing an organometallic compound, wherein $R^1$ or $R^3$ is phenyl group, or phenyl group substituted by at least one substituent selected from the group consisting of an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 10 carbon atoms or less, halogen atom, nitro group and acetyl group.

15. The method according to claim 12 for producing an organometallic compound, wherein $Y^1$ is selected from the group consisting of oxygen, sulfur and selenium atoms.

16. The method according to claim 12 for producing an organometallic compound, wherein the neutral ligand (E) is selected from the group consisting of a tertiary phosphine and imidazolium-2-ylidene.

17. The method according to claim 12 for producing an organometallic compound, wherein the organometallic compound is represented by the general formula (4):

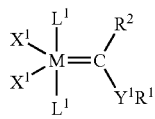 (4)

(wherein, M is elementary ruthenium or osmium; $R^1$, $R^2$, $Y^1$ and $X^1$ are each the same as the respective one described before; and $L^1$s are each a neutral electron donor, which may be the same or different).

18. The method according to claim 17 for producing an organometallic compound, wherein $R^2$ is hydrogen atom.

19. The method according to claim 17 for producing an organometallic compound, wherein
$R^1$ or $R^3$ is phenyl group, or phenyl group substituted by at least one substituent selected from the group consisting of an alkyl group of 1 to 5 carbon atoms, carboxyl group, alkoxy group of 1 to 5 carbon atoms, alkenyloxy group of 1 to 5 carbon atoms, aryloxy group of 6 to 10 carbon atoms, alkylsilyl group of 1 to 6 carbon atoms, arylsilyl group of 6 to 10 carbon atoms, acyl group of 1 to 7 carbon atoms, hydroxyl group, amino group of 10 carbon atoms or less, halogen atom, nitro group and acetyl group.

20. The method according to claim 17 for producing an organometallic compound, wherein $Y^1$ is selected from the group consisting of oxygen, sulfur and selenium atoms.

21. The method according to claim 17 for producing an organometallic compound, wherein the organometallic compound is dichloro[bistricyclohexylphosphino]phenylthiomethinoruthenium.

22. The method according to claim 17 for producing an organometallic compound, wherein the organometallic compound is free of an impurity of vinyl hetero compound or vinyl compound.

* * * * *